US00PP18130P3

(12) United States Plant Patent
Schneider

(10) Patent No.: US PP18,130 P3
(45) Date of Patent: Oct. 16, 2007

(54) *SUTERA* PLANT NAMED 'EURO 23'

(50) Latin Name: *Sutera cordata*
Varietal Denomination: Euro 23

(75) Inventor: Joshua L. Schneider, Fallbrook, CA (US)

(73) Assignee: Amerinova Properties, LLC, Bonsall, CA (US)

( * ) Notice: Subject to any disclaimer, the term of this patent is extended or adjusted under 35 U.S.C. 154(b) by 0 days.

(21) Appl. No.: 11/333,504

(22) Filed: Jan. 17, 2006

(65) Prior Publication Data

US 2007/0169241 P1 Jul. 19, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para

(57) ABSTRACT

A new and distinct cultivar of *Sutera* Plant named 'Euro 23,' particularly characterized by its lavender-pink mature flower color, compact and mounded growth habit, medium vigor, strong branching, floriferous habit, dark green foliage, and fast rooting time.

1 Drawing Sheet

The present invention relates to a new and distinct cultivar of *Sutera* plant, botanically known as *Sutera cordata,* and referred to by the variety denomination 'Euro 23'. The species is also known by the commercial name Bacopa.

The new cultivar is the product of a planned breeding program carried out by the inventor in Bonsall, Calif. The female or seed parent was *Sutera* 'Blizzard,' described in U.S. Plant Pat. No. 10,966, and characterized by its large, white flowers and spreading, vigorous habit. The male or pollen parent was *Sutera* 'Lilac King' unpatented, characterized by large lavender-pink flowers and medium vigor. The objective of the breeding program was to create new cultivars having large pink to blue flowers with a compact habit and medium vigor.

The first act of asexual reproduction of the new cultivar was accomplished when vegetative cuttings were made from the selection in October 2003 in a controlled environment in Bonsall, Calif., by or under the supervision of the inventor. Horticultural examination of controlled flowers of successive plantings has shown that the unique combination of characteristics of the new cultivar are firmly fixed and are retained through successive generations of asexual reproduction.

The new cultivar has not been observed under all possible environmental conditions. The phenotype may vary significantly with variations in environment, such as temperature, light intensity, and daylength, without, however, any variance in genotype. The following observations, measurements, and comparisons describe plants grown in Bonsall and Ojai, Calif., under normal commercial growing conditions. The age of the plant described and illustrated is nine weeks.

SUMMARY OF THE INVENTION

The following traits have been repeatedly observed, and have been determined to be basic characteristics of the new cultivar, which, in combination, distinguish the new cultivar as being new and distinct:

1. Compact, mounding growth habit.
2. Medium vigor.
3. Lavender-pink flowers.
4. Dark green foliage.
5. Fast rooting time.
6. Strong branching.

The new cultivar differs from its male parent 'Lilac King' by its lavender-pink flowers, more mounded habit, less vigor, and better branching. 'Euro 23' differs from its female parent 'Blizzard' by its lavender-pink flowers, larger blooms, and more compact habit.

BRIEF DESCRIPTION OF THE PHOTOGRAPHIC DRAWING

The photograph at the bottom of the sheet is a front view of a typical flowering plant of the new cultivar.

The photograph at the top is an enlarged view showing buds and primarily open flowers.

The colors in the photograph are as true as possible with colored reproductions of this type.

DETAILED BOTANICAL DESCRIPTION

In the following description, color references are made to The Royal Horticultural Society Colour Chart. The values are based on plant material nine weeks old grown in Bonsall and Ojai, Calif.

Botanical classification: *Sutera cordata* cv 'Euro 23'.
Seed parent: *Sutera* 'Blizzard'.
Pollen parent: *Sutera* 'Lilac King'.
Propagation:

*Type.*—Leaf cuttings. The cultivar can also be propagated by tissue culture.

*Time to initiate roots.*—Seven to ten days at 20° C.

*Time to develop roots.*—Eighteen to 24 days at temperatures of 20° C. to 25° C.

*Rooting description.*—Vigorous and fine.

*Habit.*—'Euro 23' is a low, spreading/trailing plant with indeterminate growth. Plants are perennial in mild winters (hardy to 30° Fahrenheit). Plant height is just 10 cm, but area of spread is approximately 50 cm. Growth rate is moderate, and plant vigor is very good. Overlapping lateral shoots tend to form a dense mat of foliage. No basal shoots were observed, but lateral stems will root at nodes if in contact with the soil surface. Pinching is recommended, but not required.

Lateral Shoots and Stems

The new cultivar is very free-branching, with seven main stems, each having three to four secondary shoots that tend to overlap. Lateral branch length is highly variable, averaging approximately 30 cm, and stem diameters are just 0.2 cm. Internodes are 1.6 cm long. Stems are round, growing nearly horizontally, and are minutely pubescent. Stem color is 146A.

Leaves

Leaves are opposite, small, simple, and have a herbaceous scent. The quantity of leaves per lateral varies with stem length, but averages 30 leaves on the main stem. Leaves are broadly elliptical to nearly oval. They are 1.7 cm long and 1.5 cm wide.

Leaf texture is slightly rough on both sides due to tiny scattered hairs. (No true pubescence.) Leaf margins are irregularly serrate, and venation is arcuate. Both young leaves and mature leaves are 147A in color on top and bottom. Vein color is 147B on both sides.

Petiole length is 0.4 cm and petiole width is 0.2 cm. Petioles are slightly rough with a few scattered hairs. Petiole color is 147B on top and bottom. No stipules, tendrils, spines, or prickles were observed.

Foliage forms a dense mat of leaves and overlapping laterals. Stems grow horizontally with leaf lamina twisting to face skyward, with leaves becoming progressively smaller toward shoot tips.

Flowers

Flower arrangement is solitary, axillary, and tending to cluster at the shoot tips as new buds develop from new growth. Flower form is round, salverform. Plants are floriferous. There are usually two axillary flowers open per shoot tip, and approximately 30 open flowers per main stem. Each lateral stem also has approximately 70 visible buds, and plants flower continuously on new growth. There are more than 700 flowers per plant, and flowering is indeterminate.

Flower buds are 0.6 cm long and 0.3 cm in diameter just before opening. Flowers open in four to five days. Bud color is 76D. Flowers are held upward and outward on horizontal stems, and are obovate in shape.

The flowers are small, lobed, and trumpet-shaped. They are 1.1 cm in total diameter, and 0.8 cm in height. Flower longevity is approximately seven days, and flowers are persistent. Petals are arranged in one whorl of five petals, fused at the base. Petal lobes are round, smooth on both sides, and entire. Petal lobes are 0.4 cm long and 0.3 cm wide.

Young flowers open an almost white, very light lavender purple 76D on top and bottom of petals. Mature flowers are a somewhat darker 76C on the topside of petals, and 76D below. The topside color fades to 76D. The throat of mature flowers is a bright gold, 23A. The short floral tube is 23C/D.

Sepals are minutely pubescent, arranged in one whorl of five. Sepals are lanceolate, margins are entire, tips are acute, and sepals are fused at their bases to form a shallow cup. Sepal lobes are 0.3 cm long and 0.1 cm wide. Both sides are a little rough. Both the immature and mature sepals are 146A on top and bottom.

The calyx consists of five free sepal tips with fused bases, resulting in a star-like shape. Total calyx length is 0.5 cm. Calyx diameter is 0.4 cm.

The flower pedicels are 0.5 cm long and 0.1 cm wide. The axillary flowers project from the stem axis at a 45° angle. Pedicels are minutely pubescent, and pedicel color is 144D.

Each flower has four stamens with tiny (0.1 cm) oval anthers. Anther color is 14A. Pollen is very scarce and color is 14A when present. Each flower has one pistil that is 0.7 cm long. Stigmas are round, 144B in color. Styles are 0.5 cm and 144C in color. Ovary color is 144A.

When 'Euro 23' is in bloom, there are many small, lavender-pink flowers with golden-yellow throats. Because the leaves are opposite, and flowers are axillary, flowers tend to occur in two ranks along the stems. No seeds or fruits were observed.

I claim:

1. A new and distinct cultivar of *Sutera* Plant named 'Euro 23,' as illustrated and described.

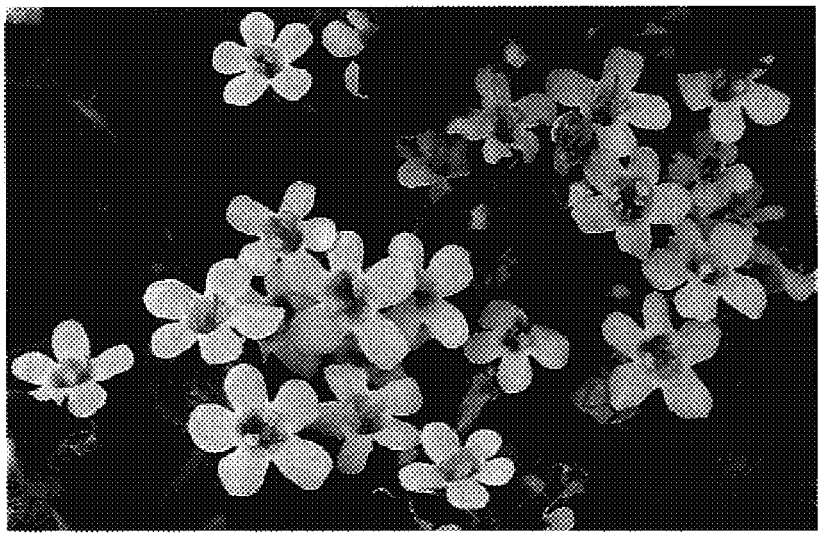
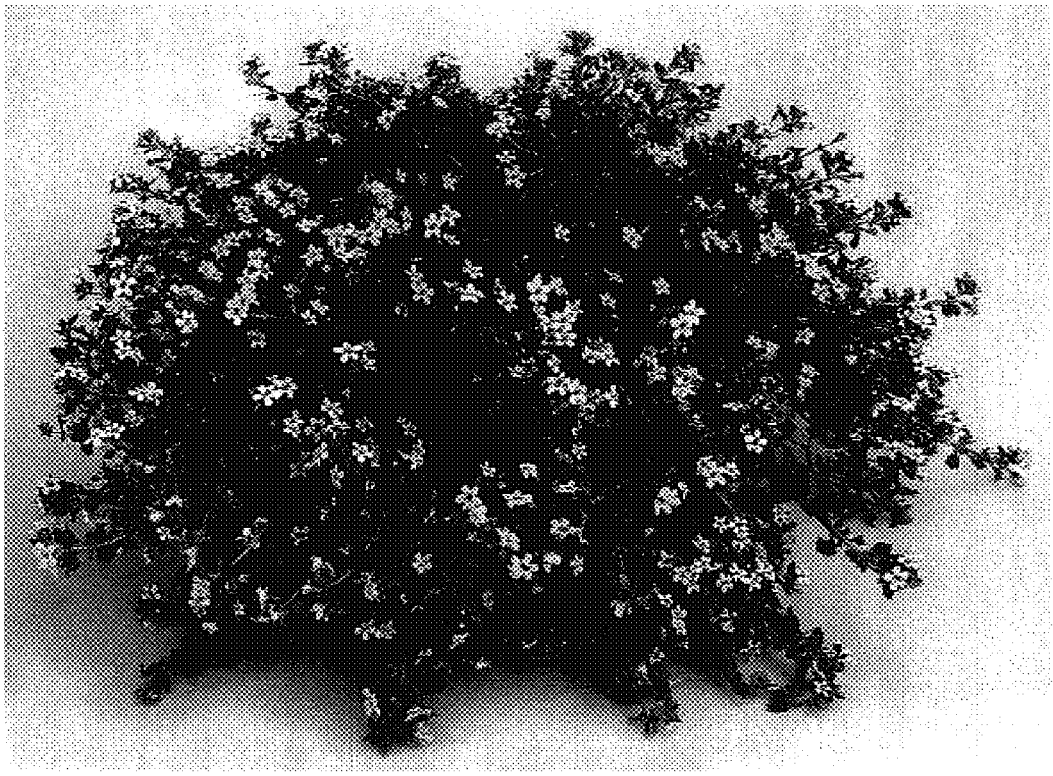

* * * * *